United States Patent [19]

Gold et al.

[11] Patent Number: 4,477,378
[45] Date of Patent: Oct. 16, 1984

[54] ESTERS OF SUBSTITUTED 8-HYDROXY-1-PHENYL-2,3,4,5-TETRAHYDRO-1H-3-BENZAZEPINES

[75] Inventors: Elijah H. Gold, West Orange; Wei K. Chang, Livingston, both of N.J.

[73] Assignee: Schering Corp., Kenilworth, N.J.

[21] Appl. No.: 416,513

[22] Filed: Sep. 9, 1982

Related U.S. Application Data

[63] Continuation of Ser. No. 118,389, Feb. 5, 1980, Pat. No. 4,349,472, which is a continuation of Ser. No. 34,048, Apr. 27, 1979, abandoned.

[51] Int. Cl.³ .................... C07D 223/16; A61K 31/55
[52] U.S. Cl. .............................. 260/239 BB; 424/244
[58] Field of Search .................................. 260/239 BB

[56] References Cited

U.S. PATENT DOCUMENTS 3,393,192  7/1968  Walter et al. ................. 260/239 BB
3,409,607  11/1968  Fujimura et al. ............. 260/239 BB
3,483,185  12/1969  Tokolics et al. .............. 260/239 BB
3,686,167  8/1972  Fujimura et al. ............. 260/239 BB
4,104,379  8/1978  Gallagher et al. ............ 260/239 BB
4,197,297  4/1980  Weinstock ................... 260/239 BB Primary Examiner—Paul M. Coughlan, Jr.
Assistant Examiner—D. B. Springer
Attorney, Agent, or Firm—Gerald S. Rosen

[57] ABSTRACT

Disclosed are esters of substituted 8-hydroxy-1-phenyl-2,3,4,5-tetrahydro-1-H-3-benzazepines represented by the general formula I

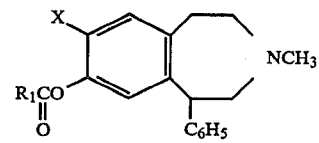

wherein X is chloro, bromo or trifluoromethyl; $R_1$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkoxy, cycloalkoxy or aryloxy; and the pharmaceutically acceptable acid addition salts thereof. The compounds show neuroleptic, antidepressive and antiaggressive activity.

20 Claims, No Drawings

ESTERS OF SUBSTITUTED 8-HYDROXY-1-PHENYL-2,3,4,5-TETRAHYDRO-1H-3-BENZAZEPINES

This is a continuation of aplication Ser. No. 118,389, filed Feb. 5, 1980, now U.S. Pat. No. 4,349,472, which in turn is a continuation of Ser. No. 34,048 filed Apr. 27, 1979, now abandoned.

This invention relates to esters of substituted 8-hydroxy-1-phenyl-2,3,4,5-tetrahydro-1H-3-benzazepines, processes for the preparation thereof, and pharmaceutical compositions containing them. The novel compounds of this invention show neuroleptic, antidepressive and antiagressive activity.

Substituted-1-phenyl-2,3,4,5-tetrahydro-1H-3-benzazepines have been previously described in the art, as for example, in U.S. Pat. No. 3,393,192, British Pat. No. 1,118,688, Danish Patent 123033, U.S. Pat. No. 3,609,138 and U.S. Pat. No. 4,011,319. The prior art has recognized that substituted-1-phenyl-2,3,4,5-tetrahydro-1H-3-benzazepines exhibit anti-bacterial effects, central nervous system effects and a hypotensive effect.

The novel compounds of this invention are the esters of substituted 8-hydroxy-1-phenyl-2,3,4,5-tetrahydro-1H-3-benzazepines of the general formula I

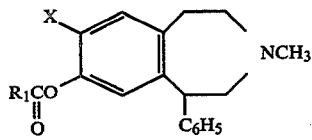

wherein X is chloro, bromo or trifluoromethyl; $R_1$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkoxy, cycloalkoxy or aryloxy;
and the pharmaceutically acceptable acid addition salts thereof.

The alkyl groups referred to above are branched or straight chain alkyl groups. $R_1$ being alkyl may contain 1 to 20 preferably 1 to 6 carbon atoms. The alkyl moiety contained in the other groups mentioned above (e.g. aralkyl, alkoxyalkyl etc.) contains 1 to 6 carbon atoms. These groups can be exemplified by methyl, ethyl, propyl, butyl, pentyl, hexyl and the corresponding branched chain isomers thereof. The alkoxy groups likewise contain 1 to 6 carbon atoms and are exemplified by methoxy, ethoxy, propoxy, butoxy, pentyloxy, hexyloxy and the branched chain isomers thereof. Preferably these groups contain 1 to 3 carbon atoms. The cycloalkyl groups referred to above contain 4 to 8 carbon atoms. The term aryl comprises unsubstituted phenyl and phenyl substituted by halogen, alkyl containing 1 to 4 carbon atoms, (preferably one carbon atom), alkoxy containing 1 to 4 carbon atoms, (preferably one carbon atom), hydroxy, nitro, trifluoromethyl or cyano.

The acid addition salts of the compounds of formula I can be derived from a variety of inorganic and organic acids such as for example sufluric, phosphoric, hydrochloric, hydrobromic, hydroiodic, methanesulfonic, sulfamic, citric, lactic, pyruvic, oxalic, maleic, stearic, succinic, tartaric, fumaric, cinnamic, aspartic, acetic, benzoic, salicylic, gluconic, ascorbic and related acids.

The compounds of formula I can be prepared by reacting a 7-x-8-hydroxy-1-phenyl-2,3,4,5-tetrahydro-1H-3-benzazepine wherein X is as defined in the compound of formula I or an alkalimetal (especially sodium) salt thereof with an acid $R_1COOH$, II, wherein $R_1$ is as defined for the compounds of formula I or a reactive derivative of the said acid. The term reactive derivative of the acid II comprises the acid halides, acid anhydrides and $R_1$— chloroformates. Preferably the compounds of formula I wherein $R_1$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, or cycloalkoxyalkyl, are prepared using an acid halide in an anhydrous aprotic solvent in the presence of an acid acceptor. Typically, acetonitrile is used as the solvent and sodium bicarbonate as the base, but a dual-function solvent such as pyridine may also be used. Other solvents include dimethylformamide and dimethylsulfoxide. Reaction temperatures and times are not critical with room temperature and 1–10 hours being preferred. The compounds of formula I wherein $R_1$ is alkoxy, aralkoxy, cycloalkoxy or aryloxy are preferably prepared by reacting the said 7-x-8-hydroxy-1-phenyl-2,3,4,5-tetrahydro-1H-3-benzazepine with the appropriate $R_1$ chloroformate in the presence of an acid acceptor in an aprotic solvent. A preferred acid acceptor is sodium hydride while a preferred solvent is dimethoxyethane. Reaction times and temperatures are also not critical with 2–24 hours and room temperatures being most preferred.

The 7-x-8-hydroxy-1-phenyl-2,3,4,5-tetrahydro-1H-3-benzazepines mentioned above as starting material can for example be prepared by dealkylation of the corresponding 8-alkoxy compounds of the general formula IV

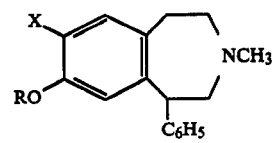

wherein R is alkyl and X is as defined for formula I. R is usually methyl but may also be any alkyl group containing e.g. up to 5 carbon atoms.

To cleave the alkoxy group and provide the hydroxy group at position 8, the compound of formula IV may be reacted with a strong acid, such as for example aqueous hydrogen halide, preferably hydrogen bromide, or sulfuric acid.

The reaction can advantageously be performed under a nitrogen atmosphere. The reaction is usually carried out in an aqueous medium (e.g. using 48 percent aqueous hydrobromic acid) at about 75° to 100° C., preferably at reflux temperature of the reaction mixture, for about 2 to 24 hours.

Other typical dealkylating procedures are the use of sodium ethanethiolate in an aprotic solvent such as dimethylformamide at 100°–120° C. for 4–6 hours, or the use of pyridine hydrochloride at 200°–240° C. for 1–2 hours.

Compound IV may be prepared by cyclization of a compound of the general formula III

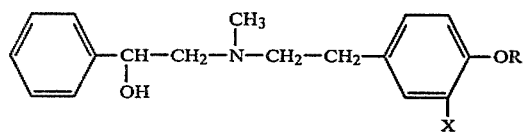

wherein X and R are as defined for formula IV. The compound of formula III can be cyclized utilizing a dehydrating agent such as for example polyphosphoric acid, sulfuric acid, methane sulfonic acid, methane sulfonic acid/P$_2$O$_5$, zinc chloride and hydrogen fluoride. Especially preferred are sulfuric acid, methane sulfonic acid, methane sulfonic acid/P$_2$O$_5$, and hydrogen fluoride maintained at about −10° to 20° C.

A convenient way for preparing a compound of the general formula III comprises the reaction of a 2-phenylethylamine with epoxyethylbenzene

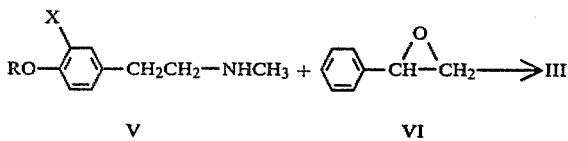

in a polar aprotic solvent such as acetonitrile, pyridine, dimethylformamide or dimethyl sulfoxide. The temperature at which the reaction is conducted is not critical, with room temperature to reflux being preferred.

Compound IV can also be prepared by introduction of the desired 7-substituent into an 8-alkoxy-1-phenyl-2,3,4,5-tetrahydro-1H-3-benzazepine containing no substituent or a replaceable substituent in position 7.

Compound IV can also be prepared by N-methylation of a corresponding 8-alkoxy-1-phenyl-2,3,4,5-tetrahydro-1H-3-benzazepine

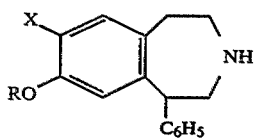

wherein R and X are as defined before. This N-methylation is accomplished in a conventional manner, a particularly facilitative method being the condensation of the compound of formula VII with formaldehyde and formic acid. Alternatively, methyl chloride or methyl bromide may be used to methylate the compound. The compound of formula X can be prepared by known methods, for example analogously to the methods described above for the preparation of compound IV.

The compounds of formula I, as well as of formulae IV and VII and of the 8-hydroxy analog of the compound of formula IV contain as asymmetric carbon atom in position 1 (chiral center). By the above described processes racemic mixture of the relevant (R)- and (S)- isomers are obtained. Separation of the isomers can be effected by the usual well known techniques. If an (R)- or (S)- isomer of the compound of formula IV or VII is used as starting material in the preparation of the desired compound I, the corresponding isomer of the compound I is obtained by the dealkylation described above.

The (R)- and (S)- isomers can be resolved by techniques such as for example resolution by means of forming an adduct (e.g. of urea), chromatography, crystallisation from optically active solvents, resolution via diastereoisomeric salts (e.g. by means of N-acetyl-D-leucine), resolution by enzymatic processes (including destruction and chemical transformation of one isomer) and destruction of one isomer. It is preferred to use fractional crystallization.

The compounds of formula I can be transformed into pharmaceutically acceptable acid addition salts by reaction with a pharmaceutically acceptable acid or a reactive derivative thereof. Also the compounds of formula I in their free form can be set free from their acid addition salts.

The compounds of this invention are typically formulated into conventional pharmaceutical compositions according to accepted procedures. The dosage of these compounds is dependent upon various factors, such as the particular compound employed and the patient's individual response. Preferably, the compositions will contain the active ingredient in an active but non-toxic amount selected from about 0.8 mg to about 200 mg of active ingredient per dosage unit.

The pharmaceutical carrier employed in the formulation of such compositions may be a solid or liquid. Typical carriers include, but are not limited to: sugars such as lactose, sucrose, mannitol and sorbitol, starches such as tapioca starch and potato starch; cellulose derivatives such as sodium carboxymethylcellulose, ethyl cellulose and methyl cellulose, gelatine; calcium phosphates such as dicalcium phosphate and tricalcium phosphate; sodium sulfate; calcium sulfate, polyvinyl alcohols; stearic acid; alkaline earth metal stearates such as calcium stearate; stearic acid vegetable oils such as peanut oil, cottonseed oil, sesame oil, olive oil and corn oil; non-ionic, cationic and anionic surfactants; ethylene glycol polymers, β-cyclodextrin; fatty alcohols and hydrolyzed cereal solids; as well as other non-toxic compatible fillers, binders, disintegrants and lubricants commonly used in pharmaceutical formulations. For injectable solutions sterile water and other steril ingredients have to be used.

Antipsychotic drugs are widely used e.g. in the treatment of schizophrenia. Their use is generally limited by their propensity to cause neurologic, autonomic and/or endocrine side effects. The compounds of this invention are novel antipsychotic drugs. The compounds have effects common to standard antipsychotic drugs but may be regarded as having a more generally better biological profile. Representative compounds of the invention have been found to have specific antipsychotic, antiaggression and antidepressant activity with low potential for producing extrapyramidal, autonomic and hormonal side-effects; the compounds did not show sedative and anti-convulsant activity. On this basis the compounds of this invention are useful agents for the treatment of manifestations of psychotic disorders due to their combination of neuroleptic, antidepressant and antiaggressive properties. The compounds are thus indicated for reducing excitement, hypermotility, abnormal initiative, affective tension and agitation through their inhibitory effects on psychomotor functions of the treated subjects. In particular these compounds are indicated as useful in the treatment of schizophrenia, mental depression, anxiety and hyperactive agitated behavioral states, particularly in mentally retarded patients.

The compounds of the invention may be co-administered intravenously with a narcotic to produce neuroleptic analgesia. Such a state provides sufficient CNS action to permit certain procedures (e.g. bronchoscopy x-ray studies, burn dressing, cystoscopy) to be performed without additional medication. Addition of inhaled nitrous oxide to the neuroleptic-narcotic combination would provide analgesia sufficient for surgical operations.

The daily dosage of the active ingredient is dependent upon various factors, such as the particular compound employed, the condition for which the compound is administered and the patient's individual response. Typical dosages for use as a neuroleptic, antidepressant or antiaggressive agent, especially in the treatment of schizophrenia, mental depression, anxiety and hyperactive agitated behavioral states, particularly in mentally retarded patients, would vary from about 0.1 to 15, preferably 0.5 to 10 mg/kg per day divided in 3 or 4 doses, administered orally or parenterally.

The neuroleptic, antidepressant and antiaggressive properties of the compounds of this invention may be ascertained by testing in standardized assays such as are described in Barnett, et al., Psychopharmacologia (Berl.) 36, 281–290 (1974)*. (S)-8-(1-adamantanecarbonyloxy)-7-chloro-3-methyl-1-phenyl-2,3,4,5-tetrahydro-1H-3-benzazepine, has an $ED_{50}$ of 17 mg/kg in the anti-muricide assay and an $ED_{50}$ of 3.0 mg/kg in the metamphetamine reversal assay. For this compound the $LD_{50}$(oral dose in mice) is greater than 100 mg/kg.

Of the compounds defined by formula I above and its acid addition salts, those compounds are preferred wherein $R_1$ is alkyl, cycloalkyl, alkoxy, aryloxy, aralkoxy, aryl, aryloxyalkyl or 1-adamantyl, especially those wherein X is chloro. In particular compounds are preferred which have the (S)-stereochemical configuration, *The properties of the compounds of this invention can be illustrated by the following test results: at position 1. Among these compounds are:

(S)-7-chloro-3-methyl-1-phenyl-8-propionyloxy-2,3,4,5-tetrahydro-1H-3-benzazepine, (m.p. 233°–234° C.)*, (S)-7-chloro-3-methyl-1-phenyl-8-phenoxyacetoxy-2,3,4,5-tetrahydro-1H-3-benzazepine, (m.p. 197°–199° C.)*, (S)-8-benzoyloxy-7-chloro-3-methyl-1-phenyl-2,3,4,5-tetrahydro-1H-3-benzazepine, (m.p. 257°–258° C.)*, (S)-7-chloro-3-methyl-1-phenyl-8-p-toluoyloxy-2,3,4,5-tetrahydro-1H-3-benzazepine, (m.p. 249°–251° C.),** and (S)-8-(1-adamantanecarbonyloxy)-7-chloro-3-methyl-1-phenyl-2,3,4,5-tetrahydro-1H-3-benzazepine and the pharmaceutically acceptable acid addition salts thereof. (The melting points given above relate to the hydrochlorides, when marked by *), and the hydrochloride ethanolate, when marked by **), respectively).

The following Examples illustrate the preparation of the novel compounds of this invention.

The following formulations illustrate some of the dosage forms in which the compounds of this invention may be employed. (Compound A mentioned in the formulation examples is (S)-8-(1-adamantanecarbonyloxy)-7-chloro-3-methyl-1-penyl-2,3,4,5-tetrahydro-1H-3-benzazepine.)

EXAMPLE 1

(S)-7-chloro-3-methyl-1-phenyl-8-propionyloxy-2,3,4,5-tetrahydro-1H-3-benzazepine hydrochloride A. reflux for 16 hours, a solution of 21.0 g (0.113 moles) of 2-(3-chloro-4-methoxyphenyl)ethylamine and 13.6 g (0.113 moles) of epoxyethylbenzene in 75 ml of acetonitrile. Remove the solvent and triturate the residue with 30 ml of ether. Filter and digest the precipitate twice with 60 ml of isopropyl ether and obtain N-[2-(3-chloro-4-methoxyphenyl)ethyl]-2-phenyl-2-hydroxyethylamine, m.p. 95°–96° C.

B. Add in small portions, 12.0 g (0.0394 moles) of the product of step A to 60 ml of concentrated sulfuric acid with cooling (ice bath) and stirring so that the temperature of the reaction mixture stays at 10°±5° C. Stir at 10° C. for 30 minutes, then for another hour at 25° C. Pour onto 500 g of ice, and then carefully add 100 ml of concentrated ammonium hydroxide, following this with the careful addition of 30 g of solid sodium hydroxide with cooling in an ice-bath, not allowing the temperature to rise above 30° C. Extract with 300 g ml of benzene. Separate the benzene layer and dry over anhydrous sodium sulfate. Remove the solvent to obtain (R,S)-7-chloro-8-methoxy-1-phenyl-2,3,4,5-tetrahydro-1H-3-benzazepine as a pale yellow syrup. Prepare the acid maleate in ethanol and recrystallize this crude salt from ethanol to obtain an analytically pure sample, m.p. 171°–173° C.

C. Heat to reflux to dissolve a mixture of 9.60 g (0.033 moles) of the product of step B and 5.80 g (0.033 moles) of N-acetyl-D-leucine in 180 ml of acetonitrile. Cool slowly to room temperature. Filter and recrystallize the salt repeatedly from acetonitrile to obtain (S)-7-chloro-8-methoxyl-1-phenyl-2,3,4,5-tetrahydro-1H-3-benzazepine N-acetyl-D-leucinate, m.p. 171°–173° C. $[\alpha]_D^{26} = +27.7°$ (c=1, ethanol). Stir 1 g of this salt in a mixture of 20 ml of 0.5 N sodium hydroxide and 20 ml of ether to total dissolution. Separate the ether layer, dry over anhydrous sodium sulfate, and evaporate to obtain (S)-7-chloro-8-methoxy-1-phenyl-2,3,4,5-tetrahydro-1H-3-benzazepine as a colorless solid. Recrystallize from ethyl ether to obtain an analytically pure sample, m.p. 81°–82° C., $[\alpha]_D^{26} = +38.3°$ (c=1, ethanol).

D. Reflux for 4 hours, a solution of 52.0 g (0.18 moles) of the product of step C in a mixture of 96 ml of 37% formaldehyde and 144 ml of 90% formic acid. Distill almost to dryness at 100° C. under reduced pressure (about 100 mm). Dissolve the residue in a mixture of 500 ml of 1 N sodium hydroxide and 500 ml of ethyl ether with cooling and stirring. Separate the ether layer, dry over anhydrous sodium sulfate, and evaporate to give (S)-7-chloro-8-methoxy-3-methyl-1-phenyl-2,3,4,5-tetrahydro-1H-3-benzazepine as a colorless solid. Obtain an analytically pure sample by crystallization from ethyl ether, m.p. 91°–92° C., $[\alpha]_D^{26} = +47.3°$(c=1, ethanol).

E. Heat and stir a mixture of 0.850 g (0.0028 moles) of the product of step D in 12 ml of 48% hydrobromic acid at 100° C. for 16 hours. Dilute with 75 ml of water and heat on a steam bath to dissolve. Adjust to about pH 8 with solid sodium bicarbonate, filter, and wash the resulting precipitate with water. Recrystallize from ethanol to obtain analytically pure (S)-7-chloro-8-hydroxy-3-methyl-1-phenyl-2,3,4,5-tetrahydro-1H-3-benzazepine, m.p. 188°–189° C., $[\alpha]_D^{26} = +44.8°$ (c=1, dimethylformamide).

F. Reflux a mixture of 6.70 g (0.0232) moles of (S)-7-chloro-8-hydroxy-3-methyl-1-phenyl-2,3,4,5-tetrahydro-1H-3-benzazepine, 8.0 g of anhydrous sodium bicarbonate and 6.0 ml of propionyl chloride in 150 ml of dry acetonitrile with stirring for 2.5 hours and concentrate to dryness on a steam bath. Dissolve the residue in a mixture of 60 ml of water and 70 ml of ethyl ether. Separate the ether layer, dry over anhydrous sodium sulfate, filter and evaporate to dryness. Redissolve the residue in 150 ml of anhydrous ethyl ether and precipitate (S)-7-chloro-3-methyl-1-phenyl-8-propionyloxy-2,3,4,5-tetrahydro-1H-3-benzazepine hydrochloride by slow addition of a slight excess of 1N ethereal hydrogen chloride. Obtain an analytical sample by crystallization from 2-propanol, m.p. 234°–236° C., $[\alpha]_D^{26} = +32.5°$ (c=1, dimethylformamide).

EXAMPLE 2

(S)-8-benzoyloxy-7-chloro-3-methyl-1-phenyl-2,3,4,5-tetrahydro-1H-3-benzazepine hydrochloride Reflux for 5 hours with stirring a mixture of 1.20 g (0.00417 moles) of (S)-7-chloro-8-hydroxy-3-methyl-1-phenyl-2,3,4,5-tetrahydro-1H-3-benzazepine (obtained in step E of Example 1), 2.0 ml (0.017 moles) of benzoyl chloride and 2.5 g of anhydrous sodium bicarbonate in 40 ml of dry acetonitrile. Evaporate to dryness on a steam bath under reduced pressure (about 100 mm). Dissolve the residue by stirring for 2 hours at 10° C. in a mixture of 50 ml each of water and ethyl ether. Separate the ether layer, dry over anhydrous sodium sulfate, and evaporate to dryness. Redissolve the residue in 50 ml of anhydrous ethyl ether and precipitate (S)-8-benzoyloxy-7-chloro-3-methyl-1-phenyl-2,3,4,5-tetrahydro-1H-3-benzazepine hydrochloride with 1N ethereal hydrogen chloride. Obtain an analytical sample by crystallization from 2-propanol, m.p. 257°–258° C., $[\alpha]_D^{26} = +10.0°$ (c=1, dimethylformamide).

EXAMPLE 3

(S)-7-chloro-8-ethoxycarbonyloxy-3-methyl-1-phenyl-2,3,4,5-tetrahydro-1H-3-benzazepine hydrochloride Add 430 mg (0.01 moles) of sodium hydride (50% in minerl oil) in small portions, to a stirred suspension of 2.88 g (0.01 moles) of (S)-7-chloro-8-hydroxy-3-methyl-1-phenyl-2,3,4,5-tetrahydro-1H-3-benzazepine (obtained in step E of Example 1) in 60 ml of dry dimethoxyethane and stir until the evolution of gas ceases. Add dropwise a solution of 1.08 g (0.01 moles) of ethyl chloroformate in 10 ml of dimethoxyethane with stirring and then stir the reaction mixture at room temperature for 16 hours. Evaporate to dryness at 100° C. and treat the residue with a mixture of 50 ml each of water and ethyl ether. Dry the ether layer over anhydrous sodium sulfate and precipitate (S)-7-chloro-8-ethoxycarbonyloxy-3-methyl-1-phenyl-2,3,4,5-tetrahydro-1H-3-benzazepine hydrochloride with 1N ethereal hydrogen chloride. Obtain an analytical sample by crystallization from 2-propanol, m.p. 196°–197° C., $[\alpha]_D^{26} = +27.1°$ (c=1, dimethylformamide).

In a manner analog to the method and Examples described above also other compounds of this invention, in free form or in the form of their salts, can be prepared, such as for example:

(S)-8-acetoxy-7-chloro-3-methyl-1-phenyl-2,3,4,5-tetrahydro-1H-3-benzazepine,(m.p. 236°–238° C.)*,
(S)-7-chloro-3-methyl-1-phenyl-8-propionyloxy-2,3,4,5-tetrahydro-1H-3-benzazepine, (m.p. 233°–234° C.)*,
(S)-8-butyryloxy-7-chloro-3-methyl-1-phenyl-2,3,4,5-tetrahydro-1H-3-benzazepine, (m.p. 248°–250° C.)*,
(S)-7-chloro-8-isobutyryloxy-3-methyl-1-phenyl-2,3,4,5-tetrahydro-1H-3-benzazepine, (m.p. 266°–268° C.)*,
(S)-7-chloro-3-methyl-1-phenyl-8-valeryloxy-2,3,4,5-tetrahydro-1H-3-benzazepine, (m.p. 244°–246° C.)*,
(S)-7-chloro-8-isovaleryloxy-3-methyl-1-phenyl-2,3,4,5-tetrahydro-1H-3-benzazepine, (m.p. 261°–263° C.)*,
(S)-7-chloro-3-methyl-1-phenyl-8-pivaloyloxy-2,3,4,5-tetrahydro-1H-3-benzazepine, (m.p. 205°–208° C.)**,
(S)-7-chloro-8-decanoyloxy-3-methyl-1-phenyl-2,3,4,5-tetrahydro-1H-3-benzazepine, (m.p. 201°–202° C.)*,
(S)-8-(1-adamantanecarboxyloxy)-7-chloro-3-methyl-1-phenyl-2,3,4,5-tetrahydro-1H-3-benzazepine, (m.p. 275°–278° C.)*,
(S)-7-chloro-8-cyclopentanecarbonyloxy-3-methyl-1-phenyl-2,3,4,5-tetrahydro-1H-3-benzazepine, (m.p. 265°–267° C.)*,
(S)-7-chloro-3-methyl-1-phenyl-8-phenoxyacetoxy-2,3,4,5-tetrahydro-1H-3-benzazepine, (m.p. 297°–199° C.)*,
(S)-8-benzoyloxy-7-chloro-3-methyl-1-phenyl-2,3,4,5-tetrahydro-1H-3-benzazepine, (m.p. 257°–258° C.)*,
(S)-7-chloro-3-methyl-1-phenyl-8-p-toluoyloxy-2,3,4,5-tetrahydro-1H-3-benzazepine, (m.p. 249°–251° C.)3*,
(S)-7-chloro-8-p-chlorobenzoyloxy-3-methyl-1-phenyl-2,3,4,5-tetrahydro-1H-3-benzazepine, (m.p. 246°–249° C.)3*,
(S)-7-chloro-8-methoxybenzoyloxy-3-methyl-1-phenyl-2,3,4,5-tetrahydro-1H-3-benzazepine, (m.p. 246°–248.5° C.)*,
(S)-7-chloro-3-methyl-8-p-nitrobenzoyloxy-1-phenyl-2,3,4,5-tetrahydro-1H-3-benzazepine, (m.p. 247°–249° C.)*,
(S)-7-chloro-8-p-cyanobenzoyloxy-3-methyl-1-phenyl-2,3,4,5-tetrahydro-1H-3-benzazepine, (m.p. 246°–247° C.)*,
(S)-7-chloro-8-methoxycarbonyloxy-3-methyl-1-phenyl-2,3,4,5-tetrahydro-1H-3-benzazepine, (m.p. 160°–165° C.)4*,
(S)-7-chloro-8-ethoxycarbonyloxy-3-methyl-1-phenyl-2,3,4,5-tetrahydro-1H-3-benzazepine, (m.p. 196°–197° C.)*,
(S)-7-chloro-3-methyl-8-phenoxycarbonyloxy-1-phenyl-2,3,4,5-tetrahydro-1H-3-benzazepine, (m.p. 234°–236° C.)*,
(S)-8-benzyloxycarbonyloxy-7-chloro-3-methyl-1-phenyl-2,3,4,5-tetrahydro-1H-3-benzazepine, (m.p. 130°–132° C.)5* as well as corresponding 7-bromo and 7-trifluoromethyl compounds.

(The melting points given above relate to salts of the respective compounds: (*) hydrochloride, (**) hemifumarate, (3*) hydrochloride ethanolate, (4*) hydrochloride hemihydrate, (5*) hydrocloride propanolate.

FORMULATION 1

|  | mg/core |
|---|---|
| Enteric Coated Tablets | |
| Compound A | 100.0 |
| Citric Acid | 1.0 |
| Lactose, USP | 33.5 |
| Dicalcium Phosphate | 70.0 |
| Nonionic Surfactant (*Pluronic F-68) | 30.0 |
| Sodium Lauryl Sulfate | 15.0 |
| Polyvinylpyrrolidine | 15.0 |
| Polyethylene Glycol (*Carbowax 1500) | 4.5 |
| Polyethylene Glycol (Carbowax 6000) | 45.0 |

| | mg/core |
|---|---|
| Denatured Alcohol 50 ml/1000 cores | |
| Corn Starch | 30.0 |
| Dry | |
| Sodium Lauryl Sulfate | 3.0 |
| Magnesium Stearate | 3.0 |
| Tablet Weight | 350.0 |

[*Pluronic and Carbowax are Registered Trade Marks]

PROCEDURE

Compound A is mixed with the citric acid, lactose, dicalcium phosphate, the pluronic and sodium lauryl sulfate. The above mixture is screened through a No. 60 screen and damp granulated with an alcoholic solution consisting of polyvinylpyrrolidone, carbowax 1500 and 6000. Add additional alcohol, if necessary, to bring powders to a pasty mass. Add corn starch and continue mixing until uniform granules are formed. Pass through a No. 10 screen, tray and dry in an oven at 100° C. for 12-14 hours. Reduce dried granulation through a No. 16 screen, add sodium lauryl sulfate and magnesium stearate, mix and compress into desired shape or a tablet machine.

COATING

The above cores are treated with a lacquer and dusted with talc to prevent moisture adsorption. Sub-coat layers are added to round out the core. A sufficient number of lacquer coats are applied to make the core enteric. Additional sub-coats and smoothing coats are applied to completely round out and smooth the tablet. Color coats are applied until desired shade is obtained. After drying the coated tablets are polished to give the tablets an even gloss.

FORMULATION 2

| Capsules | mg/capsule |
|---|---|
| Compound A | 100.00 |
| Citric Acid | 1.00 |
| Nonionic Surfactant (Pluronic, F-68) | 40.00 |
| Sodium Lauryl Sulfate | 20.00 |
| Lactose | 238.00 |
| Magnesium Stearate | 1.00 |
| | 400.00 |

PROCEDURE

Mix together Compound A, citric acid, pluronic, sodium lauryl sulfate and lactose. Pass through a No. 80 screen. Add magnesium stearate, mix and encapsulate into two-piece gelatin capsules of an appropriate size.

FORMULATION 3

| Suppository | mg/2 gms |
|---|---|
| Compound A | 100 |
| Theobroma Oil, Pharm. Grade to make | 2 gms |

PROCEDURE

Prepare a slurry of the Compound A with a portion of the melted theobroma oil and pass the slurry through a suitable colloid mill until it is free of grittiness. Add sufficient melted theobroma oil to bring the batch to final weight. Pour the melted mix, while maintaining uniformity, into appropriately prepared molds and allow to cool.

TEST DESCRIPTIONS

Anti-muricide assay: Male Long Evans rats weighing 225-250 g are housed 1 rat per cage, and killers (rats show an instinctive mouse killing behavior (muricide)) are selected initially after being deprived of food for approximately 66 hours. This is the only time the rats are deprived of food. Food, ad libitum, is available on the cage floor since food bins are not practical because they afford a hiding place for mice. The rats are tested for muricidal behavior the following day and once a week thereafter; non-killers are always eliminated. A non-killer is a rat which fails to kill a mouse placed into his cage within 5 minutes. Drugs are tested in the afternoon of the day following this weekly check for persistance of the killing behavior. Since the rats are not deprived of food or water and rarely attempt to eat the mouse, this behavior is not motivated by hunger. Four weeks after the first test for killing, the rats are injected, i.p., with placebo and then tested 30/60 minutes after the injection. Rats that do not kill are eliminated. Only rats that consistantly kill mice placed in their home cages are used for drug testing. Every treatment-group is comprised of 5 rats. Each rat is presented with a CFI male albino mouse at 30 and 60 minutes after the intraperitoneal injection (1 ml/kg) of test drug. Blockade of muricidal behavior is determined by observing the number of surviving mice 5 minutes after being introduced into the rat cages. The result is expressed in $ED_{50}$ values, which means that at the given dosage 50% of the tested rats do not kill mice.

Methamphetamine reversal assay: Groups of 10 mice are aggregated in a 11×26×13 cm plastic chamber. Test drugs are given orally thirty minutes prior to an intraperitoneal administration of methamphetamine at 15 mg/kg. (This dose of methamphetamine is about 1.5 times the $LD_{50}$ under these conditions and usually kills at least 90 percent of the animals.) As a control perphenazine at 1 mg/kg is used.(this dose of perphenazine usually affords complete protection.) The number of deaths in each group are counted 4 hours later

We claim:

1. Esters of substituted 8-hydroxy-1-phenyl-2,3,4,5-tetrahydro-1-H-3-benzazepines represented by the general formula I

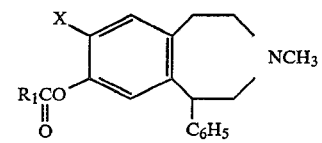

wherein X is chloro, bromo or trifluoromethyl; $R_1$ is branched or straight chain alkyl of 1 to 20 carbon atoms, unsubstituted-phenylalkyl wherein the alkyl is branched or straight chain of 1 to 6 carbon atoms, substituted-phenylalkyl wherein the alkyl is branched or straight chain of 1 to 6 carbon atoms and the substituents on the phenyl are halogen, straight or branched chain alkyl of 1 to 4 carbon atoms, straight or branched chain alkoxy of 1 to 4 carbon atoms, hydroxy, nitro, trifluoromethyl or cyano, unsubstituted phenyl or substituted phenyl wherein the substituents are halogen, straight or branched chain alkyl or 1 to 4 carbon atoms, straight or branched chain alkoxy of 1 to 4 carbon atoms, hydroxy, nitro, trifluoromethyl or cyano, alkoxyalkyl wherein the alkoxy moiety is straight or branched chain of 1 to 6 carbon atoms and the alkyl moiety is straight or branched chain of 1 to 6 atoms, aryloxyalkyl wherein the aryl moiety is unsubstituted phenyl or substituted phenyl wherein the substituents on the phenyl are halogen, straight or branched chain alkyl of 1 to 4 carbon atoms, straight or branched chain alkoxy of 1 to 4 carbon atoms, hydroxy, nitro, trifluoromethyl or cyano, and wherein the alkyl moiety is branched or straight chain with 1 to 6 carbon atoms, aralkoxyalkyl wherein the aralkoxy moiety is unsubstituted-phenylalkoxy wherein the alkoxy is branched or straight chain of 1 to 6 carbon atoms or substituted-phenylalkoxy wherein the alkoxy is branched or straight chain of 1 to 6 carbon atoms and the substituents on the phenyl are halogen, straight or branched chain alkyl of 1 to 4 carbon atoms, straight or branched chain alkoxy of 1 to 4 carbon atoms, hydroxy, nitro, trifluoromethyl or cyano and the alkyl moiety is branched or straight chain of 1 to 6 carbon atoms, cycloalkylalkyl wherein the cycloalkyl moiety is of 4 to 8 carbon atoms and the alkyl moiety is straight or branched chain of 1 to 6 carbon atoms, alkoxycarbonylalkyl wherein the alkoxy moiety is straight or branched chain of 1 to 4 carbon atoms and the alkyl moiety is straight or branched chain of 1 to 6 carbon atoms, cycloalkyl of 4 to 8 carbon atoms, cycloalkoxyalkyl wherein the cycloalkoxy moiety is of 4 to 8 carbon atoms and the alkyl moiety is straight or branched chain of 1 to 6 carbon atoms, straight or branched chain alkoxy of 1 to 6 carbon atoms, aralkoxy as defined hereinabove or aryloxy as defined hereinabove; and the pharmaceutically acceptable acid addition salts thereof.

2. A compound according to claim 1 wherein X is as defined in claim 1 and $R_1$ is branched or straight chain alkyl of 1 to 6 carbon atoms, cycloalkyl as defined in claim 1, straight or branched chain alkoxy of 1 to 3 carbon atoms, aryloxy wherein the aryl moiety is unsubstituted-phenyl or substituted-phenyl wherein the substituents are halogen, methyl, methoxy, hydroxy, nitro, trifluoromethyl or cyano, aralkoxy wherein the aryl moiety is unsubstituted-phenyl, substituted-phenyl wherein the substituents are halogen, methyl, methoxy, hydroxy, nitro, trifluoromethyl or cyano and the alkyl moiety is straight or branched chain of 1 to 3 carbon atoms, unsubstituted-phenyl or substituted-phenyl wherein the substituents are halogen, methyl, methoxy, hydroxy, nitro, trifluoromethyl or cyano, aryloxyalkyl wherein the aryl moiety is as defined hereinabove and the alkyl moiety is a straight or branched chain of 1 to 6 carbon atoms.

3. A compound according to claim 1 or 2, wherein X is chloro.

4. A compound according to claim 1 selected from the group consisting of
(S)-7-chloro-3-methyl-1phenyl-8-propionyloxy-2,3,4,5-tetrahydro-1H-3-benzazepine,
(S)-7-chloro-3-methyl-1-phenyl-8-phenoxyacetoxy-2,3,4,5-tetrahydro-1H-3-benzazepine,
(S)-8-benzoyloxy-7chloro-3-methyl-1-phenyl-2,3,4,5-tetrahydro-1H-3-benzazepine,
(S)-7-chloro-3-methyl-1-phenyl-8-p-toluoyloxy-2,3,4,5-tetrahydro-1H-3-benzazepine, or the pharmaceutically acceptable acid addition salts thereof.

5. A compound of claim 1 which is (S)-8-acetoxy-7-chloro-3-methyl-1-phenyl-2,3,4,5-tetrahydro-1H-3-benzazepine, or the pharmaceutically acceptable acid addition salts thereof.

6. A compound of claim 1 which is (S)-8-butyryloxy-7-chloro-3-methyl-1-phenyl-2,3,4,5-tetrahydro-1H-3-benzazepine, or the pharmaceutically acceptable acid addition salts thereof.

7. A compound of claim 1 which is (S)-7-chloro-8-isobutyryloxy-3-methyl-1-phenyl-2,3,4,5-tetrahydro-1H3-benzazepine, or the pharmaceutically acceptable acid addition salts thereof.

8. A compound of claim 1 which is (S)-7-chloro-3methyl-1-phenyl-8-valeryloxy-2,3,4,5-tetrahydro-1H-3-benzazepine, or the pharmaceutically acceptable acid addition salts thereof.

9. A compound of claim 1 which is (S)-b 7-chloro-8-isovaleryloxy-3-methyl-1-phenyl-2,3,4,5-tetrahydro-1H-3benzazepine, or the pharmaceutically acceptable acid addition salts thereof.

10. A compound of claim 1 which is (S)-7-chloro-3-methyl-1-phenyl-8-pivaloyloxy-2,3,4,5-tetrahydro-1H-3-benzazepine, or the pharmaceutically acceptable acid addition salts thereof.

11. A compound of claim 1 which is (S)-7-chloro-8-decanoyloxy-3-methyl-1-phenyl- 2,3,4,5-tetrahydro-1H-3-benzazepine, or the pharmaceutically acceptable acid addition salts thereof.

12. A compound of claim 1 which is (S)-7-chloro-8-cyclopentanecarbonyloxy-3-methyl-1-phenyl-2,3,4,5-tetrahydro-1H- 3-benzazepine, or the pharmaceutically acceptable acid addition salts thereof.

13. A compound of claim 1 which is (S)-7-chloro-8-p-chlorobenzoyloxy-3-methyl-1-phenyl-2,3,4,5-tetrahydro-1H-3-benzazepine, or the pharmaceutically acceptable acid addition salts thereof.

14. A compound of claim 1 which is (S)-7-chloro-8-p-methoxybenzoyloxy-3-methyl-1-phenyl-2,3,4,5-tetrahydro-1H-3-benzazepine, or the pharmaceutically acceptable acid addition salts thereof.

15. A compound of claim 1 which is (S)-7-chloro-3-methyl-8-p-nitrobenzoyloxy-1phenyl-2,3,4,5-tetrahydro-1H-3-benzazepine, or the pharmaceutically acceptable acid addition salts thereof.

16. A compound of claim 1 which is (S)-7-chloro-8-p-cyanobenzoyloxy-3-methyl-1-phenyl-2,3,4,5-tetrahydro-1H-3-benzazepine, or the pharmaceutically acceptable acid addition salts thereof.

17. A compound of claim 1 which is (S)-7chloro-8-methoxycarbonyloxy-3-methyl-1-phenyl-2,3,4,5-tetrahydro-1H-3-benzazepine, or the pharmaceutically acceptable acid addition salts thereof.

18. A compound of claim 1 which is (S)-7-chloro-8-ethoxycarbonyloxy-3-methyl-1-phenyl-2,3,4,5-tetrahydro-1H-3-benzazepine, or the pharmaceutically acceptable acid addition salts thereof.

19. A compound of claim 1 which is (S)-7-chloro-3-methyl-8-phenoxycarbonyloxy-1-phenyl-2,3,4,5-tetrahydro-1H-3-benzazepine, or the pharmaceutically acceptable acid addition salts thereof.

20. A compound of claim 1 which is (S)-8-benzyloxycarbonyloxy-7-chloro-3-methyl-1-phenyl-2,3,4,5-tetrahydro-1H-3-benzazepine, or the pharmaceutically acceptable acid addition salts thereof.

* * * * *